United States Patent
Watson et al.

(10) Patent No.: US 6,533,759 B1
(45) Date of Patent: Mar. 18, 2003

(54) FLASH CHAMBER WITH A SELF CLOSING VALVE FOR USE WITH A CATHETER

(76) Inventors: Robert Watson, 1704 Singletree, Bowling Green, KY (US) 42103; Mark Bartlett, 924 Old Orchard, Garland Road, TX (US) 75041

( * ) Notice: Subject to any disclaimer, the term of this patent is extended or adjusted under 35 U.S.C. 154(b) by 0 days.

(21) Appl. No.: 09/872,348

(22) Filed: Jun. 1, 2001

Related U.S. Application Data

(60) Provisional application No. 60/208,690, filed on Jun. 1, 2000.

(51) Int. Cl.[7] .............................................. A61M 5/178
(52) U.S. Cl. ........................... 604/167.02; 604/164.01; 604/164.07; 604/167.06; 604/168.01; 604/170.02
(58) Field of Search ................................. 604/110, 158, 604/159, 161, 164.01, 164.02, 164.04, 164.07, 165.01, 165.02, 165.04, 167.01, 167.02, 167.06, 168.01, 170.01, 170.02

(56) References Cited

U.S. PATENT DOCUMENTS

| | | | |
|---|---|---|---|
| 3,859,998 A | | 1/1975 | Thomas et al. |
| 4,772,264 A | | 9/1988 | Cragg |
| 4,813,938 A | * | 3/1989 | Raulerson .................. 604/156 |
| 4,842,591 A | * | 6/1989 | Luther ............................ 285/3 |
| 5,013,304 A | | 5/1991 | Russell et al. |
| 5,032,116 A | | 7/1991 | Peterson et al. |
| 5,092,845 A | | 3/1992 | Chang |
| 5,098,395 A | | 3/1992 | Fields |
| 5,188,611 A | * | 2/1993 | Orgain ......................... 604/192 |
| 5,320,602 A | * | 6/1994 | Karpiel ......................... 600/101 |
| 5,338,303 A | * | 8/1994 | King et al. .................. 604/110 |
| 5,352,205 A | | 10/1994 | Dales et al. |
| 5,401,249 A | * | 3/1995 | Shields ......................... 604/110 |
| 5,584,812 A | | 12/1996 | Martin |
| 5,688,253 A | * | 11/1997 | Paradis .................. 604/164.01 |
| 5,697,914 A | | 12/1997 | Brimhall |
| 5,704,914 A | | 1/1998 | Stocking et al. |
| 5,749,857 A | | 5/1998 | Cuppy |
| 5,755,696 A | * | 5/1998 | Caizza .................. 604/164.11 |
| 5,755,709 A | | 5/1998 | Cuppy |
| 5,891,105 A | * | 4/1999 | Mahurkar .................... 604/110 |
| 6,074,370 A | * | 6/2000 | Pressly et al. .............. 604/110 |
| 6,123,688 A | * | 9/2000 | Botich et al. ................ 604/110 |
| 6,179,812 B1 | * | 1/2001 | Botich et al. ................ 604/110 |
| 6,183,440 B1 | * | 2/2001 | Bell ............................... 604/110 |
| 6,224,575 B1 | * | 5/2001 | Garvin ......................... 604/110 |
| 6,235,003 B1 | * | 5/2001 | Dysarz ........................ 604/110 |

* cited by examiner

Primary Examiner—Ira S. Lazarus
Assistant Examiner—Andrea M. Ragonese
(74) Attorney, Agent, or Firm—James Daly, IV; Joan L. Simunic; Middleton Reutlinger

(57) ABSTRACT

A flash chamber having a self-closing valve for use with a catheter is described. The flash chamber, which is connected to the catheter, precludes blood leakage as a needle is removed from the catheter and an IV unit is coupled to the catheter. The flash chamber permits the practitioner to visually verify that a blood vessel has been punctured and includes a self-sealing valve that prevents blood from flowing out of the flash chamber as the needle is removed and the IV unit is attached.

20 Claims, 4 Drawing Sheets

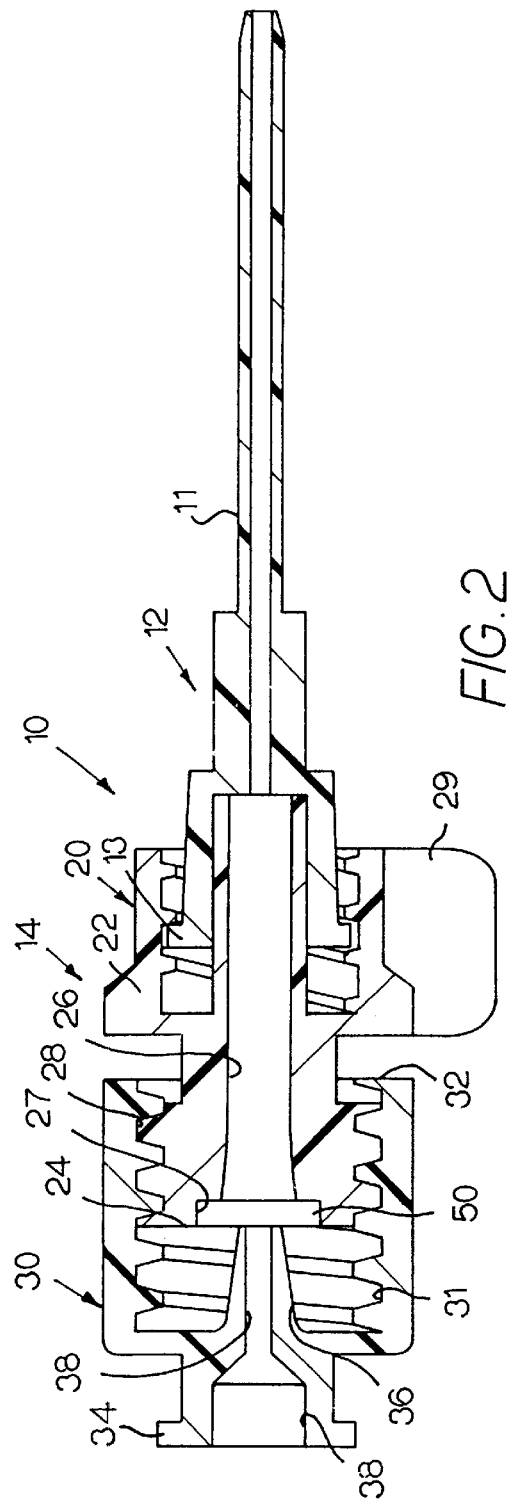

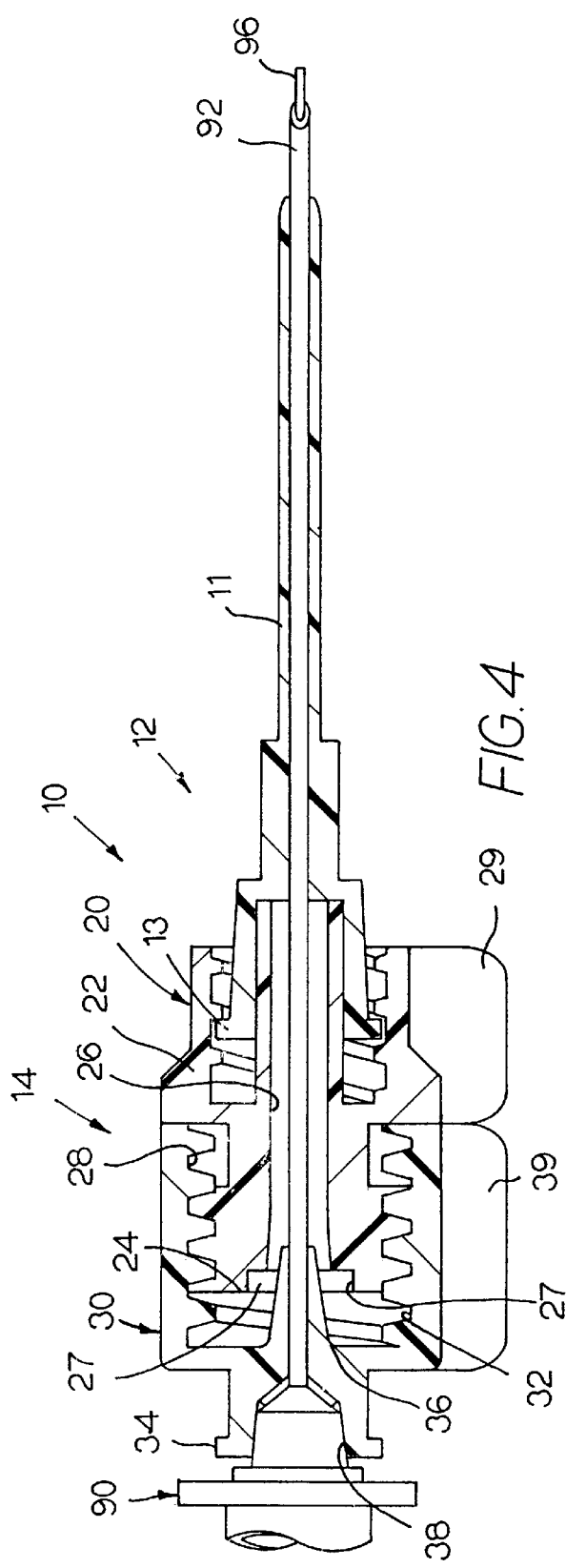
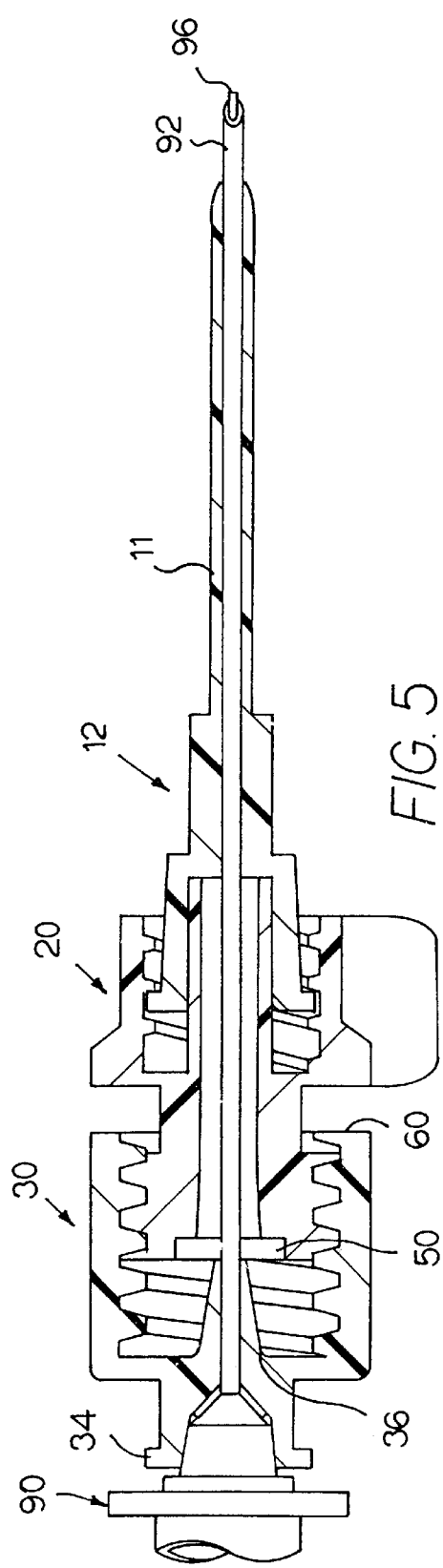

FLASH CHAMBER WITH A SELF CLOSING VALVE FOR USE WITH A CATHETER

CROSS-REFERENCE TO RELATED PATENT APPLICATIONS

This application claims priority from U.S. Provisional Application Ser. No. 60/208,690, filed Jun. 1, 2000, which application is incorporated herein by reference in its entirety.

BACKGROUND

The present invention relates to a flash chamber with a self-closing valve for use with a catheter. The flash chamber precludes blood leakage as a catheter needle is removed from the catheter and an IV unit is coupled to the catheter.

Intravenous (IV) procedures are commonly used in the medical arts to deliver medications and other fluids to patients. Typically, the IV procedure is initiated by having a needle encircled by a catheter or plastic sleeve pierce a patient's skin. The needle and catheter are then inserted into a vein or artery to provide the practitioner with access to the circulatory system. The needle is then removed from the catheter, and an IV line is attached to a terminal hub.

When the needle, which is commonly attached to a syringe, is within the catheter a positive pressure is applied against the blood coursing through the punctured vein or artery so that blood remains in the blood vessel. However, once the needle is removed from the catheter and before the IV line is attached to the hub blood can freely flow from the punctured vessel through the catheter. The blood exiting the catheter obscures the working area and exposes the practitioner to direct contact with the patient's blood.

Because intravenous procedures are so common and important in the medical arts, it would be advantageous to have an IV catheter assembly designed to keep the blood from exiting through the catheter when the needle is removed and before the IV line is attached. Preferably the design should be relatively simple, thereby reducing the possibility of a failure of the system, and should be capable of being used with the current IV lines without the need for adapters.

SUMMARY OF THE PREFERRED EMBODIMENT

The present invention is for a flash chamber with a self-closing valve for use with a catheter. The flash chamber precludes blood leakage as a needle is removed from the catheter and an IV unit is coupled to the catheter. The flash chamber is connected to the catheter, and is adapted to receive the IV line. The flash chamber permits the practitioner to visually verify that a blood vessel has been punctured and includes a self-sealing valve that prevents blood from flowing out of the flash chamber as the needle is removed and the IV unit is attached. A stylus extends into the flash chamber and is positioned such that the stylus can be made to protrude through the valve placing the catheter in fluid communication with the IV unit.

DESCRIPTION OF FIGURES

FIG. 2 is a cross-sectional side view of the catheter assembly of FIG. 1 with the stylus withdrawn and the pathway closed;

FIG. 3 is a cross-sectional side view of the catheter assembly of FIG. 1 with the stylus protruding through the diaphragm, thereby leaving the pathway open;

FIG. 4 is a cross-sectional side view of the catheter assembly of FIG. 1 with the stylus protruding through the diaphragm and with a needle protruding through the catheter;

FIG. 5 is cross-sectional side view of the catheter assembly of FIG. 1 with the stylus removed from the diaphragm and with a needle protruding through the catheter;

DETAILED DESCRIPTION OF THE PREFERRED EMBODIMENT

The catheter assembly including a flash chamber with a self-closing valve depicted in the various Figures is selected solely for the purposes of illustrating the invention. Other and different catheter assemblies and flash chambers may utilize the inventive features described herein as well.

Figure 1:
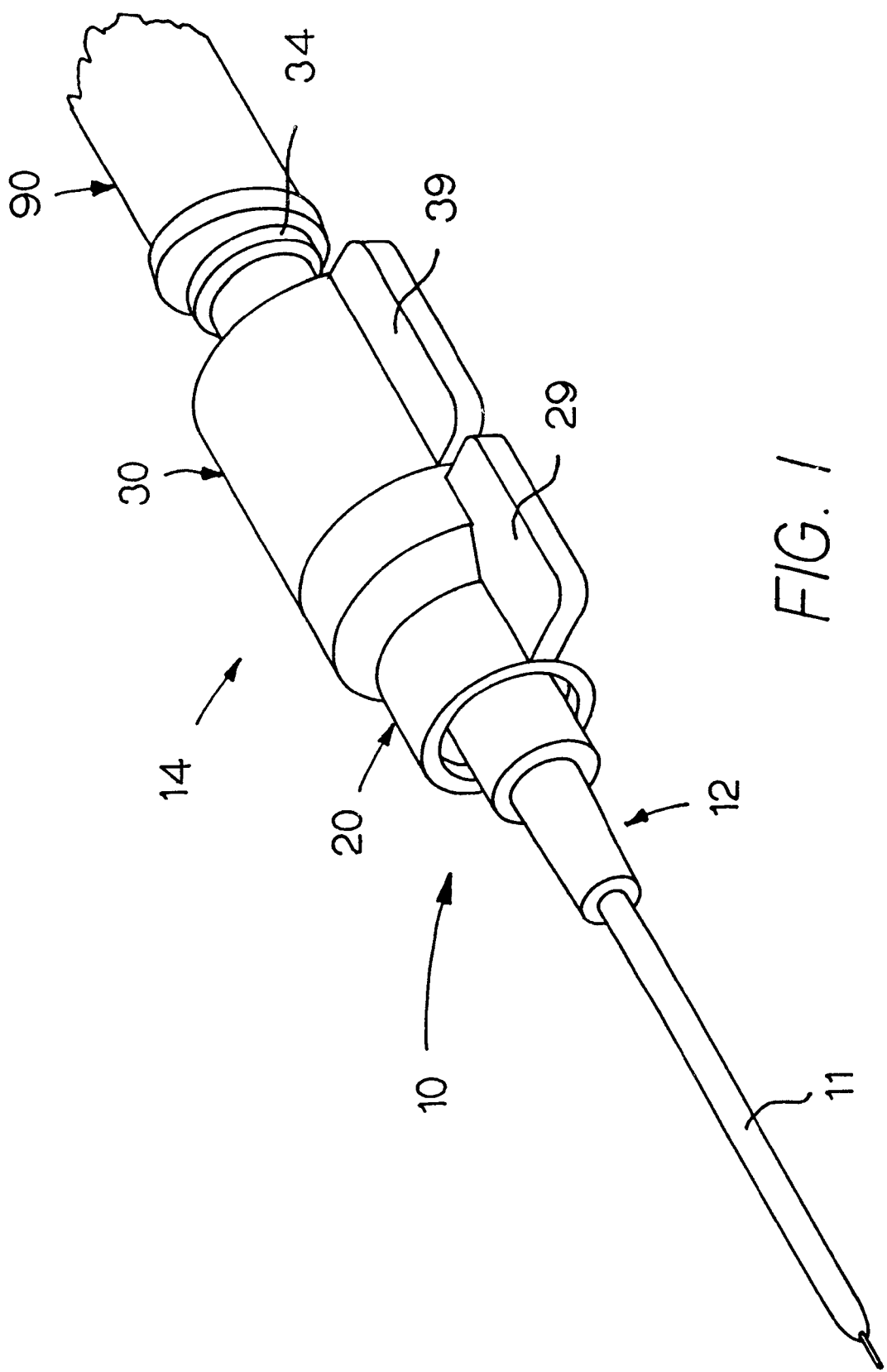
FIG. 1 is a perspective view of a catheter assembly including a flash chamber with a self-closing valve made in accordance with the present invention.

Reference is first made to FIGS. 1 through 5 in which the catheter assembly including a flash chamber with a self-closing valve constructed in accordance with the present invention is generally noted by the character numeral 10. The catheter assembly 10 has as major components a flash chamber 14, a self-closing valve 50, and a catheter 12. The catheter 12 is a hollow sleeve 11 with a hub 13, as is known in the art. The self-closing valve 50 is a diaphragm with sufficient resiliency that fluids, such as blood, cannot leak through the slit when it is closed. In a preferred embodiment, the diaphragm 50 is made of self-sealing elastomeric materials so that the diaphragm "closes" when it is in a resting state. Further, in a preferred embodiment, the diaphragm 50 is pre-slit minimizing the risk of creating shreds from the diaphragm material as the catheter 12 and needle are forced through the diaphragm 50.

Figure 6:
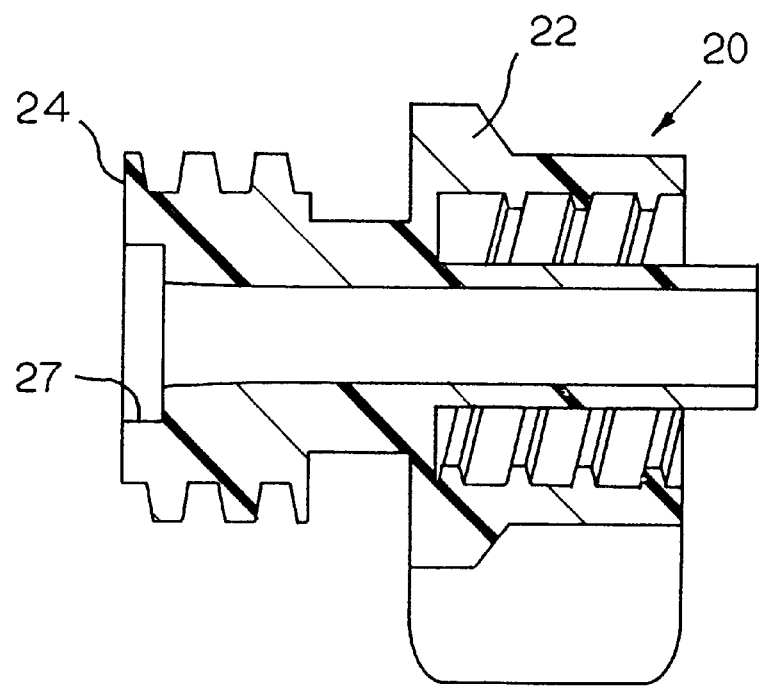
FIG. 6 is a cross-sectional side view of the first housing of the flash chamber.
Figure 7:
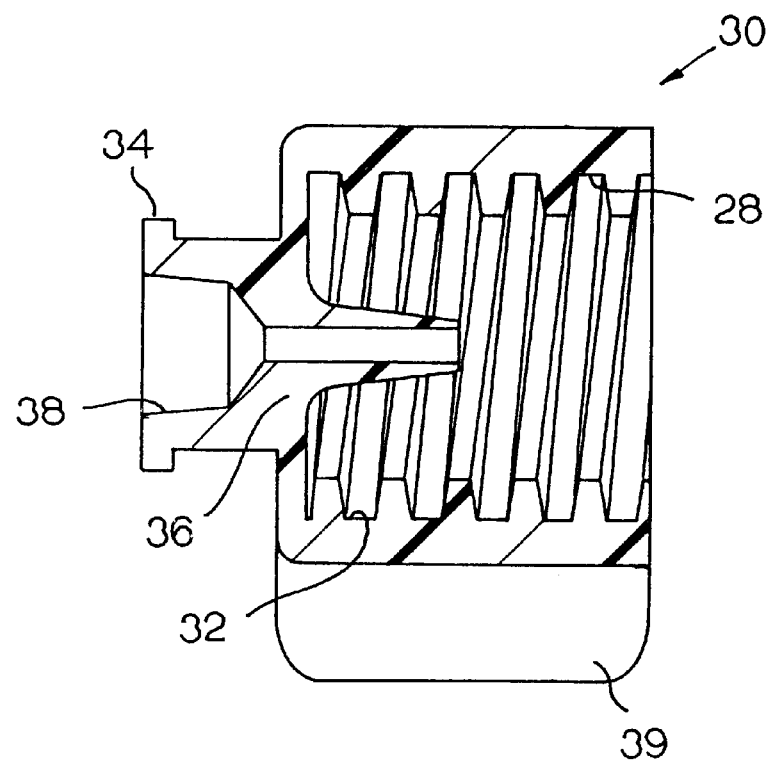
FIG. 7 is a cross-sectional side view of the second housing of the flash chamber.

As shown in FIGS. 2–7, the flash chamber 14 includes a first housing 20 and a second housing 30. The housings 20, 30 can be manufactured from any material which can be produce a semi-rigid device and which can retain the shape of the device during sterilization procedures. Because the practitioner may wish to see blood flowing into and through the housings 20, 30, optionally, the housings 20, 30 can be manufactured from an essentially translucent material. However, translucency of the material is not required for the flash chamber to function as intended.

The first housing 20 has a receiver end 22 which is adapted to reversibly receive the catheter 12, and a valve end 24 which is threaded 28 on the exterior surface. An essentially centered bore 26 extends longitudinally through the housing 20 from the receiver end 22 to the valve end 24. When the catheter 12 is attached to the first housing 20, as shown in FIGS. 2–5, the bore 26 is in fluid communication with the catheter sleeve 11. The bore 26 has a port or a section with an enlarged diameter 27 at the valve end 24 proportioned such that the self-sealing valve or diaphragm 50 can fit snuggly within the port 27.

As shown in FIGS. 2–7, the second housing 30 has an attachment end 32 with a threaded core 31, a connector 34, and a stylus 36. The attachment end 32, and more particularly the threaded core 31, is adapted to engage the threads 28 of the valve end 24 of the first housing 20. The threaded core 31 has sufficient length that the threads 28 of the first housing 20 can be screwed into the core 31 until the attachment end 32 of the second housing 30 abuts the receiver end 22 of the first housing 20 as shown, for example, in FIG. 2. The connector 34, which extends outward from the second housing 30 away from the threaded core 32, is adapted to receive a standard luer-lok syringe or intravenous (IV) tube connection, as are known in the art. The stylus 36 projects from the connector 34 into the threaded core 32 and has an essentially centered bore 38. As shown in FIGS. 4 and 5, near the threaded core end of the stylus, the bore 38 has a diameter sufficient to receive an injection needle 92. Near the connector end, the bore 38 is enlarged to allow the needle end 94 of a syringe 90 to be received within the bore 38.

The first housing 20 is attached to the second housing 30 by engaging the threads 28 of the valve end 24 with the threaded core 31 of the attachment end 32. As shown in FIGS. 3 and 4, the housings 20, 30 can be tightened until the first housing 20 abuts the second housing 30, and the stylus 36 protrudes through the diaphragm 50. This defines an "open" position for the catheter assembly 10, with the stylus bore 38 in fluid communication with the first housing bore 26 and the catheter 12. When the catheter assembly 10 is open, fluids can flow through the intravenous tubing into the flash chamber 19, then into the catheter 12, and then into the patient's circulatory system. Because the stylus 36 is in direct contact with the diaphragm 50, it is preferable but not required that the stylus 36 be slightly blunted so that the stylus 36 does not scratch rubber shreds from the diaphragm 50.

As shown in FIGS. 2 and 5, the catheter system 10 also has a "closed" position in which the first housing 20 is separated from the second housing 30 such that a space or gap 60 remains between the receiver end 22 and the attachment end 32. In the closed position, the housings 20, 30 are sufficiently separated so that the stylus 36 does not penetrate the diaphragm 50. As shown in FIG. 5, the stylus 36 can be removed from the diaphragm 50 but the needle 92 can remain in position through the diaphragm 50. This allows the diaphragm 50 to partially close and to form a seal around the needle 92. Then, the needle 92 can be removed allowing the diaphragm 50 to completely close, or seal, preventing blood from moving beyond the flash chamber 14. The sequential removal of the stylus 36 and then the needle 92 is not necessary for the diaphragm 50 to seal as intended, but by allowing the diaphragm 50 to close in two stages, the risk of blood leakage is further reduced. With the stylus 36 and needle 92 removed and the diaphragm 50 closed, blood can flow into the centered bore 26 allowing visual identification that the patient's blood vessel has been properly punctured. However, the blood can move no further than the diaphragm 50. In a preferred embodiment, when the catheter assembly 10 is closed, the stylus 36 abuts but does not penetrate the diaphragm 50. The presence of the stylus 36 creates a slight pressure against the diaphragm 50 to help keep the slit closed, thereby minimizing the risk of blood leakage through the diaphragm 50.

Because time can be critical in many medical procedures, particularly when an intravenous line is being inserted, it is advantageous to have a catheter assembly 10 that is easy to use. In an embodiment, the first housing 20 and second housing 30 are oriented such that by rotating the second housing 30 about 90° relative to the first housing 20 the catheter assembly 10 moves from the closed to the opened position. Thus, when an IV line is connected to the connector 34, simply rotating the second housing 30 slightly closes the gap 60 and initiates flow from the IV source to the patient's blood vessel. Optionally, stops or barricades which are known in the art may be added to the threaded core 32 and the threads 28 to limit the relative rotation of the housings 20, 30 although such stops are not required to allow the catheter assembly to function as intended. Further, optional fins 29, 39 may be added to the first and second housings 20, 30 to provide an easier finger grip for the practitioner. The fins 29, 39 can make it slightly easier to rotate the second housing 30 relative to the first housing 20, but the fins 29, 39 are not a required element of the catheter assembly 10.

In use, the catheter assembly 10 is prepared by attaching the catheter 12 to the first housing 20 of the flash chamber 14. The assembly is then opened by rotating the second housing 30 relative to the first housing 20 so that the stylus 36 protrudes through the diaphragm 50. With the diaphragm 50 forced open, the needle 92 and its associated guidewire 96 are inserted through the stylus 36 and through the catheter 12. The needle 92 is then used to puncture the patient's skin, and is positioned within the vein, or within the artery with the aid of the guidewire 96, as is known in the art. The second housing 30 is then turned to the closed position to form the gap 60. Preferably, this action is completed before removing the needle 92, as shown in FIG. 5. By removing the stylus 36 from the diaphragm 50—that is, by opening the gap 60—and then retracting the syringe 90 and needle 92 from the catheter assembly 10, the diaphragm 50 can close completely as the needle 92 is removed preventing the backflow of blood. The IV line can then be connected at the connector 32, the second housing 30 turned to close the gap 60 forcing the stylus 36 through the diaphragm 50, and the fluid flow initiated. In practice, because of the natural turning actions required to remove the syringe 90 and to connect the IV line with the connector 32, the stylus 36 tends to be removed from the diaphragm 50 as the syringe 90 is removed and it 36 is forced through the diaphragm 50 as the IV line is connected. In an alternative embodiment, the needle 92 and guidewire 96 may be supplied already inserted through the catheter assembly 10. In this case, the practitioner can simply insert the catheter in the patient's vein or artery and proceed as above.

It is understood that, in light of a reading of the foregoing description and drawings, those with ordinary skill in the art will be able to make changes and modifications to the present invention without departing from the spirit or scope of the invention, as defined herein. For example, although the embodiments presented herein anticipate that the first housing is threaded and the second housing is adapted to receive the threads of the first housing, other means which function to keep the housings together and that allow for relative axial movement between the housings may be used.

What is claimed is:

1. A flash chamber for use with a catheter, said flash chamber comprising:

a. a self-closing valve;

b. a first housing, having a receiver end and a valve end, said receiver end being adapted to reversibly receive said catheter and said valve end being adapted to receive said self-closing valve, and said first housing having a centered bore extending longitudinally from said valve end to said receiver end; and c. a second housing, having a connector, a stylus and an attachment end, said connector projecting outward and being adapted to receive an intravenous (IV) tube connection, said stylus having a centered bore to permit an injection needle to slidingly pass into and through said stylus bore and projecting from said connector toward said attachment end, and said attachment end being adapted to receive said valve end of said first housing such that said first housing can be rotated relative to said second housing between an opened position wherein said stylus protrudes through said self-closing valve and said stylus bore is in fluid communication with said first housing bore and a closed position wherein said self-closing valve forms a barrier between said stylus bore and said first housing bore.

2. The flash chamber of claim 1 wherein said self-closing valve is a diaphragm.

3. The flash chamber of claim 2 wherein said diaphragm is made of an elastomeric material.

4. The flash chamber of claim 2 wherein said diaphragm includes a slit.

5. The flash chamber of claim 1 wherein said valve end includes threads on an exterior surface.

6. The flash chamber of claim 5 wherein said attachment end is adapted to engage the threads of said valve end.

7. The flash chamber of claim 1 wherein said first housing includes an exterior fin.

8. The flash chamber of claim 1 wherein said second housing includes an exterior fin.

9. The flash chamber of claim 1 wherein said first housing is made of a translucent material.

10. The flash chamber of claim 1 wherein said second housing is made of a translucent material.

11. A catheter assembly for use in intravenous procedures, said catheter assembly comprising:
   a. a catheter, having a hollow sleeve with a hub; and
   b. a flash chamber, including
      i. a self-closing valve;
      ii. a first housing, having a receiver end and a valve end, said receiver end being adapted to reversibly receive said catheter hub and said valve end being adapted to receive said self-closing valve, and said first housing having a centered bore extending longitudinally from said valve end to said receiver end; and
      iii. a second housing, having a connector, a stylus and an attachment end, said connector projecting outward and being adapted to receive an intravenous (IV) tube connection, said stylus having a centered bore to permit an injection needle to slidingly pass into and through said stylus bore and projecting from said connector toward said attachment end, and said attachment end being adapted to receive said valve end of said first housing such that said first housing can be rotated relative to said second housing between an opened position wherein said stylus protrudes through said self-closing valve and said stylus bore is in fluid communication with said first housing bore and said catheter sleeve and a closed position wherein said self-closing valve forms a barrier between said stylus bore and said first housing bore and said catheter sleeve.

12. The flash chamber of claim 11 wherein said self-closing valve is a diaphragm.

13. The flash chamber of claim 12 wherein said diaphragm is made of an elastomeric material.

14. The flash chamber of claim 12 wherein said diaphragm includes a slit.

15. The flash chamber of claim 11 wherein said valve end includes threads on an exterior surface.

16. The flash chamber of claim 15 wherein said attachment end is adapted to engage the threads of said valve end.

17. The flash chamber of claim 11 wherein said first housing includes an exterior fin.

18. The flash chamber of claim 11 wherein said second housing includes an exterior fin.

19. The flash chamber of claim 11 wherein said first housing is made of a translucent material.

20. The flash chamber of claim 11 wherein said second housing is made of a translucent material.

* * * * *